(12) United States Patent
Hanna

(10) Patent No.: US 6,450,966 B1
(45) Date of Patent: Sep. 17, 2002

(54) METHOD FOR NON-INVASIVE BLOOD PRESSURE CUFF IDENTIFICATION USING DEFLATION PRESSURE MEASUREMENTS

(75) Inventor: D. Alan Hanna, Boulder, CO (US)

(73) Assignee: Datex-Ohmeda, Inc., Tewksbury, MA (US)

(*) Notice: Subject to any disclaimer, the term of this patent is extended or adjusted under 35 U.S.C. 154(b) by 0 days.

(21) Appl. No.: 09/563,688

(22) Filed: May 3, 2000

(51) Int. Cl.[7] ............................................. A61B 5/02
(52) U.S. Cl. .................... 600/490; 600/492; 600/494
(58) Field of Search ................................. 600/493, 481, 600/485, 490, 491, 492, 494, 495, 496, 497, 498, 499

(56) References Cited

U.S. PATENT DOCUMENTS

| | | | |
|---|---|---|---|
| 4,501,280 A | * | 2/1985 | Hood .......................... 600/490 |
| 4,729,383 A | | 3/1988 | Susi |
| 5,003,981 A | | 4/1991 | Kankkunen et al. |
| 5,022,403 A | * | 6/1991 | LaViola ....................... 600/493 |
| 5,025,793 A | | 6/1991 | Richley et al. |
| 5,060,654 A | | 10/1991 | Malkamaki et al. |
| 5,103,830 A | | 4/1992 | Shinomiya |
| 5,301,676 A | | 4/1994 | Rantala et al. |
| 5,447,160 A | | 9/1995 | Kankkunen et al. |
| 5,464,019 A | | 11/1995 | Anderson et al. |
| 5,518,000 A | | 5/1996 | Booth et al. |
| 5,626,142 A | * | 5/1997 | Marks ......................... 600/492 |
| 5,730,139 A | | 3/1998 | Miyazaki et al. |
| 6,171,254 B1 | * | 1/2001 | Skelton ........................ 600/490 |

* cited by examiner

Primary Examiner—Kevin Shaver
Assistant Examiner—Navin Natnithithadha
(74) Attorney, Agent, or Firm—Marsh Fischmann & Breyfogle LLP (57) ABSTRACT

An inventive apparatus and method as disclosed for the automatic identification of a given one of a predetermined plurality of cuff assemblies interconnectable to a sphygmomanometer for use in a blood pressure measurement procedure. The invention provides for the obtainment of a pressure measurement(s) during deflation of an inflatable cuff, and utilization of such measurement(s) to identify the cuff assembly. More particularly, each different cuff assembly may be provided with a corresponding gas-flow restrictor which allows the pressure measurement(s) made during deflation of a given cuff assembly to be correlated in fashion that allows for identification. Preferably, first and second pressure transducers are provided for automatic pressure measurements both upstream and downstream of a cuff assembly during the deflation portion of a cuff identification operation. The upstream and downstream pressure measurements may be utilized to calculate a sequence of ratio values which in turn may be employed in the cuff identification procedure.

37 Claims, 5 Drawing Sheets

METHOD FOR NON-INVASIVE BLOOD PRESSURE CUFF IDENTIFICATION USING DEFLATION PRESSURE MEASUREMENTS

FIELD OF THE INVENTION

The present invention relates to the field of non-invasive blood pressure measurement, and more particularly to a method and apparatus for automatically identifying a given one of a predetermined plurality of non-invasive blood pressure cuffs employable in a sphygmomanometric system.

BACKGROUND OF THE INVENTION

The use of automated sphygmomanometers for the measurement of blood pressure typically entails the placement of an inflatable cuff about an arterial vessel of a body appendage, e.g. the upper arm of a patient. The cuff contains an inflatable bladder which is positioned around the appendage and inflated via an air pump. The inflated bladder provides a constricting pressure against the blood inside the artery. The inflation pressure is generally established to be above a patient's systolic pressure and should serve to partially occlude the artery. After inflation, gas may be slowly bled from the inflated cuff to gradually reduce the pressure acting upon the artery. During deflation, pressure perturbations, or oscillometric pulses, generated by the partially-occluded artery may be transmitted through the cuff gas supply line for sensing. The sensed pulses may then be analyzed to allow for calculation of the systolic, diastolic and/or mean arterial pressure(s) of a patient, as well as the heart rate of a patient.

It should be noted that, if the pressure of the inflated cuff significantly exceeds a patient's systolic pressure, blood flow may be unacceptably impeded for purposes of obtaining meaningful measurements. Additionally, high inflation pressures may cause patient discomfort. On the other hand, if the cuff pressure is insufficient, arterial occlusion may be insufficient to yield oscillometric pulses in a pressure range that allows accurate measurements to be taken.

As will be appreciated, the initial inflation pressure desirable for a given patient (e.g. to achieve the desired arterial occlusion) will depend upon the physical attributes of the patient. Specifically, the desired inflation pressure will normally increase with the size of the patient.

The establishment of the desired cuff pressure is closely correlated to the size of a given cuff (e.g. the circumference thereof). It is important to use a cuff which is large enough to distribute the bladder over a relatively large surface area so that the resulting inflation pressure will be largely uniform. Thus, a properly fitted cuff on an adult will be larger than a properly fitted cuff on a child, and a properly fitted cuff on a child will be larger than a properly fitted cuff on a neonate.

In this regard, it is recognized that medical personnel will generally select the cuff size deemed most appropriate for a given patient. It is also recognized that for the given cuff size selected by medical personnel there will be a corresponding inflation pressure, or range of pressures, desirable for achieving the above-noted partial arterial occlusion appropriate for blood pressure measurement.

SUMMARY OF THE INVENTION

In view of the foregoing, a primary objective of the present invention is to provide a method and apparatus that provides for the automatic identification of a given one of a predetermined plurality of non-invasive blood pressure cuffs employed in a given blood pressure measurement procedure. Such identification facilitates selection of a desirable initial inflation pressure to be utilized in the blood pressure measurement procedure.

An additional objective of the present invention is to provide for automatic cuff identification in a manner that does not compromise the flexibility or application of the blood pressure measurement system.

Yet a further objective of the present invention is to provide for automated cuff identification in a manner that is both convenient and reliable.

One or more of the above objectives and additional advantages are realized in the inventive method and apparatus of the present invention that provide for a cuff identification operation prior to a blood pressure measurement procedure. The inventive method includes the steps of inflating, at least partially, an inflatable cuff in a pneumatic circuit by flowing gas thereinto; and deflating, at least partially, the inflatable cuff by passing at least a portion of the gas out of the inflatable cuff. The method further provides for the obtainment, during the deflating step, of at least one gas pressure measurement in the pneumatic circuit. Such gas pressure measurement may then be utilized to identify the inflatable cuff being utilized. Preferably, the gas pressure measurement is obtained downstream of the inflatable cuff.

In conjunction with the inventive method, a first pressure measurement means may be employed in the pneumatic circuit to obtain the downstream pressure measurement(s), and the deflation step may further provide for the passage of the gas through a gas-flow restriction means (e.g. a member having a shaped orifice therethrough) interconnected with the pneumatic circuit upstream from the first pressure measurement means. More particularly, the gas-flow restricting means may be located downstream from the inflatable cuff, and fixedly interconnected therewith. In the later regard, it should be noted that each of a predetermined plurality of inflatable cuffs employable with the present invention may be provided with a corresponding different one of a predetermined plurality of corresponding gas-flow restrictors, wherein each of the restrictors serves to restrict, or resist, gas flow therethrough to a differing, discernable degree, thereby facilitating automatic cuff identification.

In a related aspect of the inventive method, the deflation step may provide for both the passage of the gas through a first gas-flow restriction means that is located in the pneumatic circuit upstream from the first pressure measurement means and downstream from the inflatable cuff (e.g. fixedly interconnected therewith), and the passage of the gas through a second gas-flow restriction means interconnected with the pneumatic circuit downstream of the first pressure measurement means. The deflation step may also provide for the selective opening of a bleed valve located in the pneumatic circuit downstream of the second gas-flow restricting means, e.g., wherein the bleed valve may be controlled to provide for a gradual, linear release of gas from the pneumatic circuit. In the later regard, it should be noted that second gas-flow restricting means may actually comprise a bleed valve that is operable to provide a desired degree of gas-flow resistance when opened, thereby obviating the need for a separate gas-flow restrictor and release valve.

The inventive method may further provide for conducting at least one gas pressure measurement in the pneumatic circuit upstream of the inflatable cuff (e.g. via the use of a second gas pressure measurement means). Such upstream pressure measurement(s) may then be utilized with the downstream pressure measurement(s) to determine a measurement, e.g. a value corresponding with a ratio therebetween. In turn, such ratio value may be utilized in the cuff identification step.

In another aspect of the inventive method, the inflating step may provide for the inflation of a cuff to a degree corresponding with a first predetermined pressure (e.g. as measured by the first pressure measurement means), and the deflating step may provide for cuff deflation to a degree corresponding with at least a second predetermined pressure. The obtainment of downstream pressure measurement(s) may be terminated upon at least one of two conditions. First, the obtaining step may be terminated when the inflatable cuff has deflated to a degree corresponding with the second predetermined pressure. Alternatively, the obtaining step may be terminated when a predetermined amount of time has lapsed after initiation of the deflating step. Preferably, the obtaining step will be terminated upon the earliest of the two above-noted conditions.

In one arrangement, the inventive method provides for the obtainment of a plurality of pressure measurements both upstream and downstream of the inflatable cuff during the deflating step, such upstream and downstream pressure measurements being obtained in a synchronous , paired fashion. The pairs of upstream and downstream pressure measurements are then utilized to determine a corresponding plurality of ratio values. The plurality of ratio values may be utilized in a predetermined algorithm to determine an average ratio value, a maximum ratio value and a minimum ratio value. The average ratio value may be employed to identify the inflatable cuff being utilized, which in turn allows for the automatic selection of an appropriate initial inflation pressure to be utilized in the actual blood pressure measurement procedure that follows. In this regard, the average ratio value may be compared with predetermined reference ratio value ranges (e.g. corresponding with each potential cuff to be identified) in the cuff identification operation. For example, cuff #1 (e.g. for neonates) may have a first predetermined reference value range; cuff #2 (e.g. for children) may have a second predetermined reference value range that is greater than the first range and separated therefrom by a predetermined "guard band"; cuff #3 (e.g. for adults) may have a third predetermined ratio value range that is greater than the first and second ranges and separated from the second range by a predetermined "guard band"; and cuff #4 (e.g. for obese patients) may have a fourth predetermined ratio value range that is greater than the first, second and third ranges and separated from the third range by a predetermined "guard band". In the event that a given average ratio value falls within a "guard band", the method may provide for reinitiation of the cuff identification operation and/or termination of the operation with an indication provided to the user (e.g. a message display after a predetermined sequence of "guard band" readings).

The maximum and minimum measured ratio values may be employed to ensure the integrity of the cuff identification. That is, for example, if the difference between the maximum ratio value and the minimum ratio value exceeds a predetermined reference value, the cuff identification operation may be reinitiated and/or a corresponding indicator may be otherwise provided to a user (e.g. a display message after a predetermined number of iterations).

In accordance with the described arrangement, the inventive method may further provide for a predetermined delay period between the inflation step and the deflation step of the cuff identification operation. During such predetermined time period, gas pressure measurements may be obtained both upstream of the inflatable cuff and downstream of the inflatable cuff (e.g. via the first and second measurement means). Such measurements may then be compared to ensure the integrity of the pneumatic circuit. In the event that such comparison indicates a difference that exceeds a predetermined reference value, the method may provide for an automatic response. By way of example, such response may include the provision of an indication to a user (e.g. to check for pneumatic line kinks, etc.), reinitiation of the cuff identification operation and/or termination of the cuff identification operation.

In conjunction with the present invention, an inventive apparatus is also provided for identifying at least one inflatable cuff interconnectable to a sphygmomanometer. The apparatus comprises inflation and deflation means, interconnectable in a pneumatic circuit with an interconnectable inflatable cuff, for selectively inflating and deflating the cuff. The apparatus further includes a processor preprogrammed to automatically receive at least one pressure measurement from a first pressure measurement means in the pneumatic circuit during operation of the deflation means in a cuff identification operation. The processor is further preprogrammed to automatically employ the pressure measurement to identify the given inflatable cuff interconnected to the apparatus. Preferably, the first pressure measurement means is located in the pneumatic circuit downstream of the interconnectable cuff.

As will be appreciated, the processor means may be operatively interconnected with the inflation means and deflation means and preprogrammed to control the operation of each in the cuff identification operation. More particularly, the processor means may be preprogrammed to successively operate an air pump comprising the inflation means, and open a bleed valve comprising a deflation means.

The inventive apparatus may further include a second pressure measurement means for obtaining at least one pressure measurement in the pneumatic circuit upstream of the interconnectable inflatable cuff. The second pressure measurement means may also be interconnected with the processor means, wherein the processor is preprogrammed to automatically receive at least one upstream pressure measurement (i.e. relative to the inflatable cuff) and at least one downstream pressure measurement (i.e. relative to the inflatable cuff), and to automatically calculate a ratio therebetween. Most preferably, a plurality of upstream and downstream pressure measurements will be synchronously obtained by the processor in corresponding pairs, wherein each pair is utilized to determine a corresponding ratio value for use in cuff identification.

Of note, the interconnectable inflatable cuff may be fixedly and pneumatically attached to a first gas-flow restricting means (e.g. a gas orifice), wherein the first gas-flow restricting means restricts the flow of gas therethrough at a predetermined resistive level. In this regard, the inventive apparatus may be provided to identify any given one of a predetermined plurality of inflatable cuffs when interconnected in the pneumatic circuit, wherein each of the predetermined plurality of inflatable cuffs is fixedly and pneumatically interconnected to a corresponding one of a plurality of gas-flow restricting means, each of said gas-flow restricting means being different.

To normalize the various pressure measurements obtainable in conjunction with cuff identification, the inventive apparatus may further include a second gas-flow restricting means. More particularly, the second gas-flow restricting means may be located in the pneumatic circuit downstream of the interconnectable cuff, first gas-flow restricting means, and/or second pressure measurement means. As noted, the second gas-flow restricting means may comprise a bleed valve. When a separate restrictor and bleed valve are employed, the restrictor means may be provided upstream of the bleed valve.

In view of the foregoing, it should be appreciated that an overall inventive system may also be provided for use in obtaining blood pressure measurements. Such system may include a predetermined plurality of inflatable cuffs, each of the predetermined cuffs being fixedly and pneumatically interconnected to a corresponding one of a plurality of gas-flow restricting means, wherein each of the gas-flow restricting means restricts the flow of gas therethrough to a differing degree. The system may further include a monitor that is pneumatically interconnectable to any one of the predetermined plurality of inflatable cuffs. The monitor may house inflation means and deflation means for selectively inflating and deflating, respectively, a given, interconnected one of the predetermined plurality of inflatable cuffs. The monitor is operable to automatically identify the given connectable one of the predetermined plurality of inflatable cuffs based upon at least one pressure measurement obtained during operation of the deflation means in a cuff identification operation. The monitor may include first and second pressure measurement means, as previously noted, to obtain a corresponding plurality of upstream and downstream pressure measurements (i.e. relative to the given interconnected inflatable cuff). Outputs from the first and second pressure measurement means may then be employed (e.g. in a ratio value) to provide a relative measure of the pressure drop between the first and second pressure measurement means across the gas-flow restricting means of the given interconnected, inflatable cuff. Again, a processor may be provided for automatically controlling operation of the inflation means and deflation means, for automatically receiving measurements from the first and second pressure measurement means, and for automatically utilizing the measure values to identify the interconnected cuff.

Numerous advantages are provided by the present invention. In particular, the inventive method and apparatus accommodate the use of varying lengths of pneumatic lines to interconnect a cuff and a monitor while monitoring accuracy in cuff identification. Similarly, the present invention yields high accuracy regardless of variations in the tightness or quality of the wrap of a given cuff about a patient appendage. Similarly, accuracy of the present invention is maintained despite wear of the inflation means employed (e.g. an air pump). Finally, the present invention is relatively easy and inexpensive to implement and lends itself to a variety automated approaches for enhancing overall reliability. Numerous additional advantages and aspects of the present invention will become apparent upon consideration of the further description that follows.

DETAILED DESCRIPTION

Figure 1:
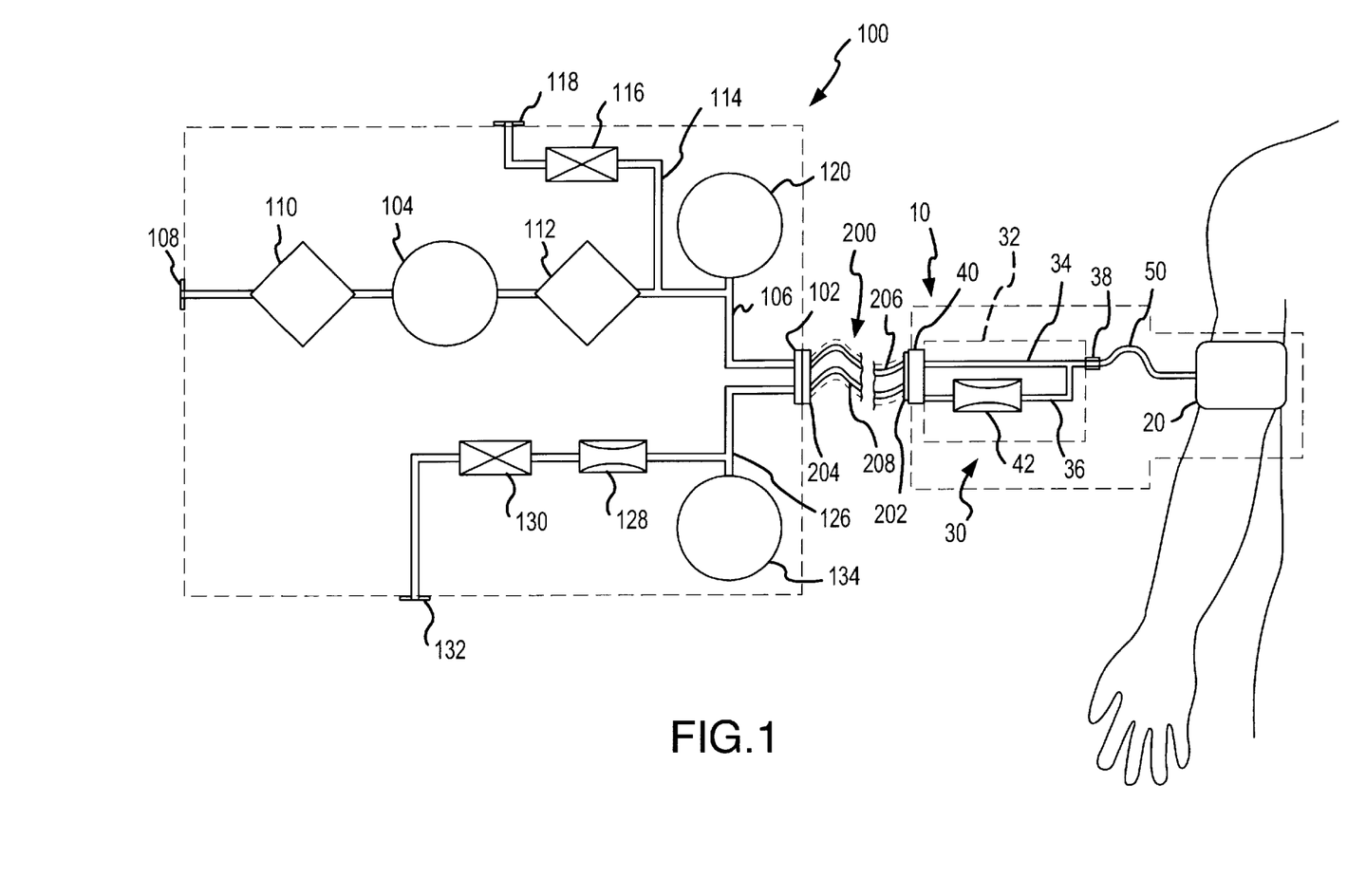
FIG. 1 schematically illustrates a pneumatic circuit of interconnected components in one embodiment of the present invention.

FIG. 1 schematically illustrates one embodiment of the present invention comprising an inflatable cuff assembly pneumatically interconnected to a monitor 100 via a dual-lumen hose 200.

Cuff assembly 10 is an exemplary one of a predetermined plurality of different cuff assemblies employable with monitor 100 in a fashion that allows monitor 100 to automatically identify the particular given cuff assembly interconnected thereto. By way of primary example, the predetermined plurality of cuff assemblies may vary in size (e.g. corresponding with obese/very large patients, normal adults, normal children, neonates) and/or corresponding intended application (e.g. arm, leg, finger, etc) and/or manufacturer. The exemplary cuff assembly 10 includes an inflatable cuff 20 sized for selective positioning about a predetermined patient appendage (e.g. an arm portion, leg portion, finger, etc.). The cuff 20 may comprise an inflatable bladder and an exterior cover adapted for bodily contact. The cuff 20 may also include a securing means (e.g. a hook and loop patch with interfacing strips) for selectively securing the cuff 20 to the intended patient appendage (e.g. via wrapping the cuff 20 about the appendage). Cuff assembly 10 further includes a cuff plug 30 pneumatically and fixedly interconnected to cuff 20 via a single-lumen line 50 (e.g. comprising soft, flexible rubber or plastic tubing) for inflating/deflating cuff 20. In other arrangements, a dual-lumen tubing could be utilized in place of the single-lumen line 50, wherein the separate lines are used for inflation and deflation.

As schematically shown in FIG. 1, cuff plug comprises a housing 32 and gas-flow circuit lines 34 and 36 which are pneumatically interconnected at a distal end for gas-flow through port 38 to/from the single-lumen line 50. Gas-flow line 34 and gas-flow line 36 each separately terminate at then proximal ends at an interconnection port 40 that is adapted for selective, pneumatic circuit interconnection/disconnection with a first connection port 202 of dual-lumen hose 200, wherein lumen 206 of hose 200 is pneumatically interconnectable to gas-flow line 34 and lumen 208 of hose 200 is pneumatically interconnectable to gas-flow line 36. In turn, a second connection port 204 of dual-lumen hose 200 may be provided for selective, pneumatic circuit interconnection/disconnection with a connection port 102 provided at monitor 100. Alternatively, port 40 of the cuff plug may be provided for direct interconnection/disconnection with port 102 of the monitor 100. As will be appreciated, ports 40, 202, 204 and 102 may be provided with registration means to facilitate the desired pneumatic interconnections upon adjoinment.

Cuff plug 30 further comprises a gas-flow restrictor 42 (e.g. a plug member having a shaped orifice) positioned in gas-flow line 36 so as to restrict the flow of gas therethrough. Gas-flow restrictor 42 functions to identify the particular interconnected cuff assembly 10. In this regard, a predetermined plurality of cuff assemblies may be utilized, wherein each of the corresponding cuff plugs is provided with a differently sized gas-flow restrictor. For example, wherein the smaller the size of the corresponding cuff 20 the greater the flow resistance provided by the corresponding gas-flow restrictor 42.

Turning now to the monitor 100 shown in FIG. 1, a gas-flow pump 104 is provided for supplying gas through a first flow line 106 to port 102 to inflate an interconnected cuff 20. More particularly, pump 104 may be selectively operated so as to draw gas (e.g. air) through an intake port 108 and particulate filter 110, and to pump such gas through a second particulate filter 112 in first flow line 106. In turn, gas pumped through first flow line 106 may flow on through the gas flow line 34 of an interconnected cuff assembly 30. Such flow may pass directly via ports 102 and 40, or via ports 102, 204, 40 and first lumen line 206 when dual lumen hose 200 is employed. The first flow line 106 may be also pneumatically interconnected via dump line 114 to a dump valve 116 within monitor 100 for selectively exhausting gas through first flow line 106 to exhaust port 118. Additionally, a gas pressure sensor 120 (e.g. a pressure transducer) may be pneumatically interconnected to first flow line 106 to selectively measure the gas pressure therewithin.

Monitor 100 further includes a second flow line 126 having one end that terminates in connection port 102. Such end of the second flow line 126 is disposed for selective pneumatic interconnection with the second lumen 208 of the dual lumen hose 200, when employed, or directly with gas-flow line 36 of cuff plug 30. As shown in FIG. 1, second flow line 126 passes through a gas-flow restrictor 128 (e.g. an orifice member) to bleed valve 130. Bleed valve 1is operable to selectively exhaust gas passing through second flow line 126 to exhaust port 132. Of note, a gas pressure sensor 134 (e.g. a pressure transducer) is pneumatically interconnected to second flow line 126, upstream from the gas-flow restrictor 128. In other embodiments, the bleed valve 130 may be provided to integrally function as gas-flow restrictor (e.g., via a controlled gas release), thereby obviating the need for restrictor 128 so as to reduce part count. In such embodiments, gas pressure sensor 134 may be located just upstream from the bleed valve 130.

As will be appreciated, the above-described cuff assembly and monitor 100, as well as dual lumen hose 200 when employed, define a pneumatic circuit in which gas is pumped through first flow line 106, first lumen 206 (if hose 200 is employed), gas-flow line 34 and line 50 to inflate cuff 20. The pneumatic circuit further provides for the flow of gas through line 50, gas-flow line 36, second lumen 208 (if hose 200 is employed), and second flow line 126 during deflation of inflatable cuff 20.

Figure 2:
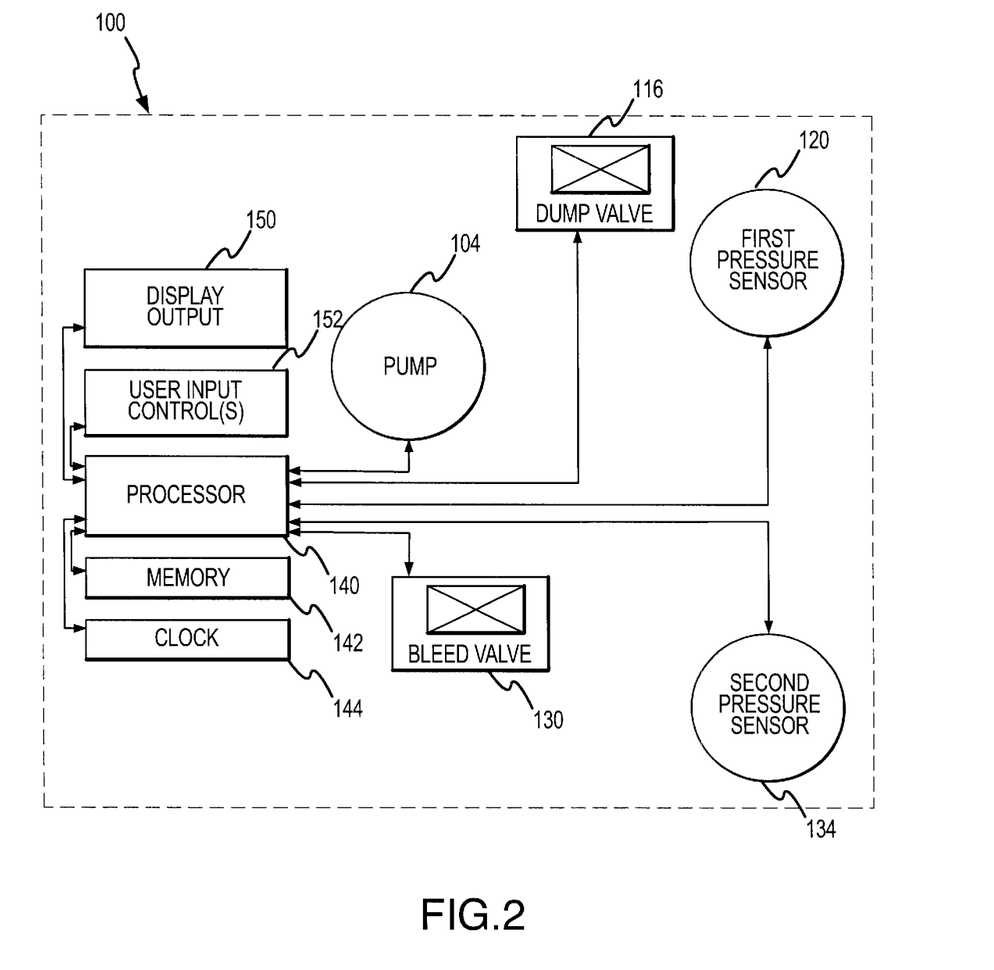
FIG. 2 presents a signal flow schematic corresponding with the embodiment of FIG. 1.

Referring now to FIG. 2, a signal flow schematic of monitor 100 is illustrated. In particular, a processor 140 is interconnected with memory 142 and clock 144 to provide for automatic control, monitoring and response to the various flow control and measurement components of monitor 100, including in particular, pump 104, the first and second pressure sensors 120 and 134, dump valve 116 and bleed valve 130. Additionally, monitor 100 may include a display output 150 and user input controls 152 to provide preprogrammed functionalities and user selected functionalities as will be described further hereinbelow.

Figure 3A:
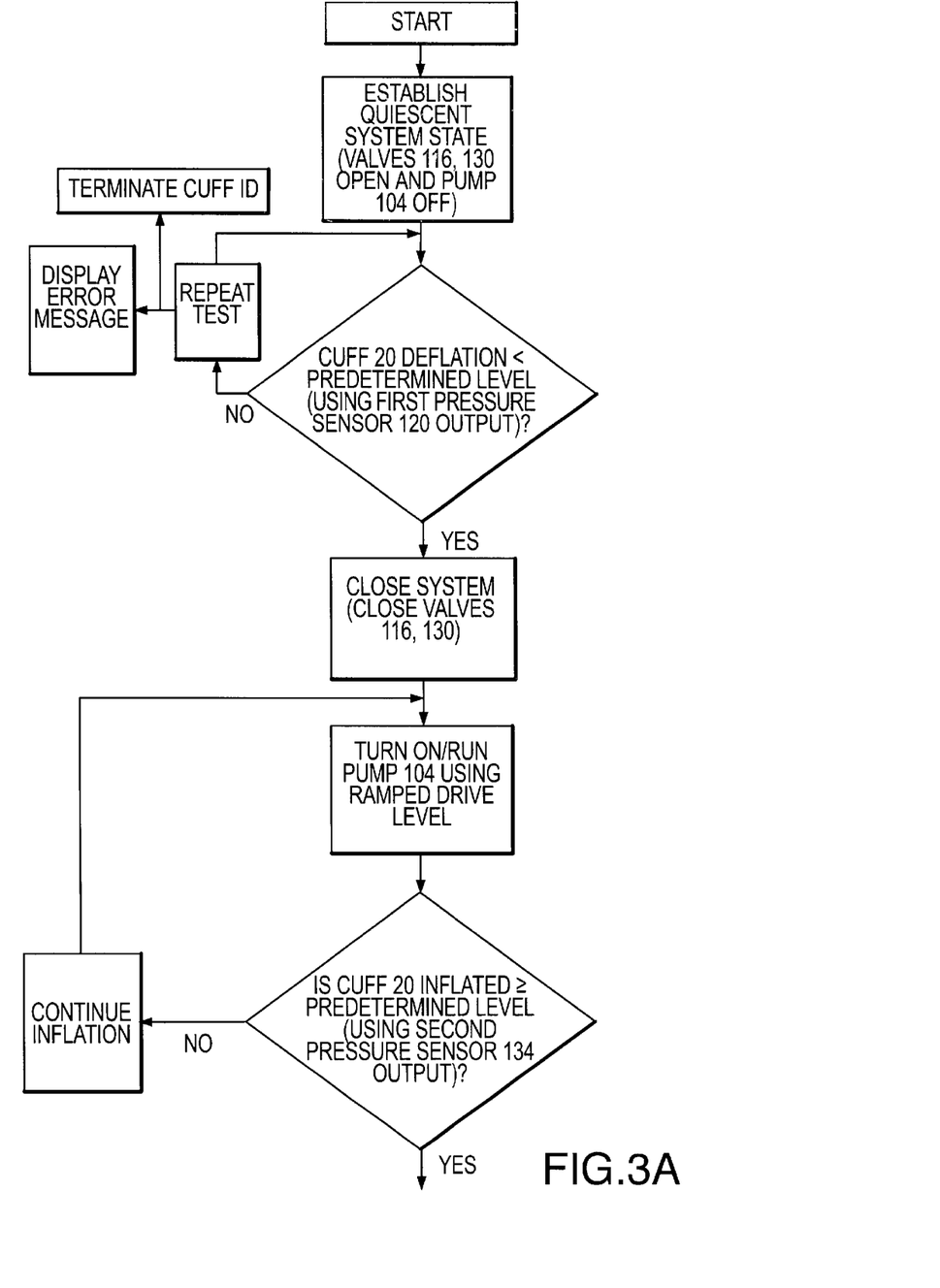
FIGS. 3A–3C present a process diagram corresponding with the operation of embodiment of FIG. 1.
Figure 3B:
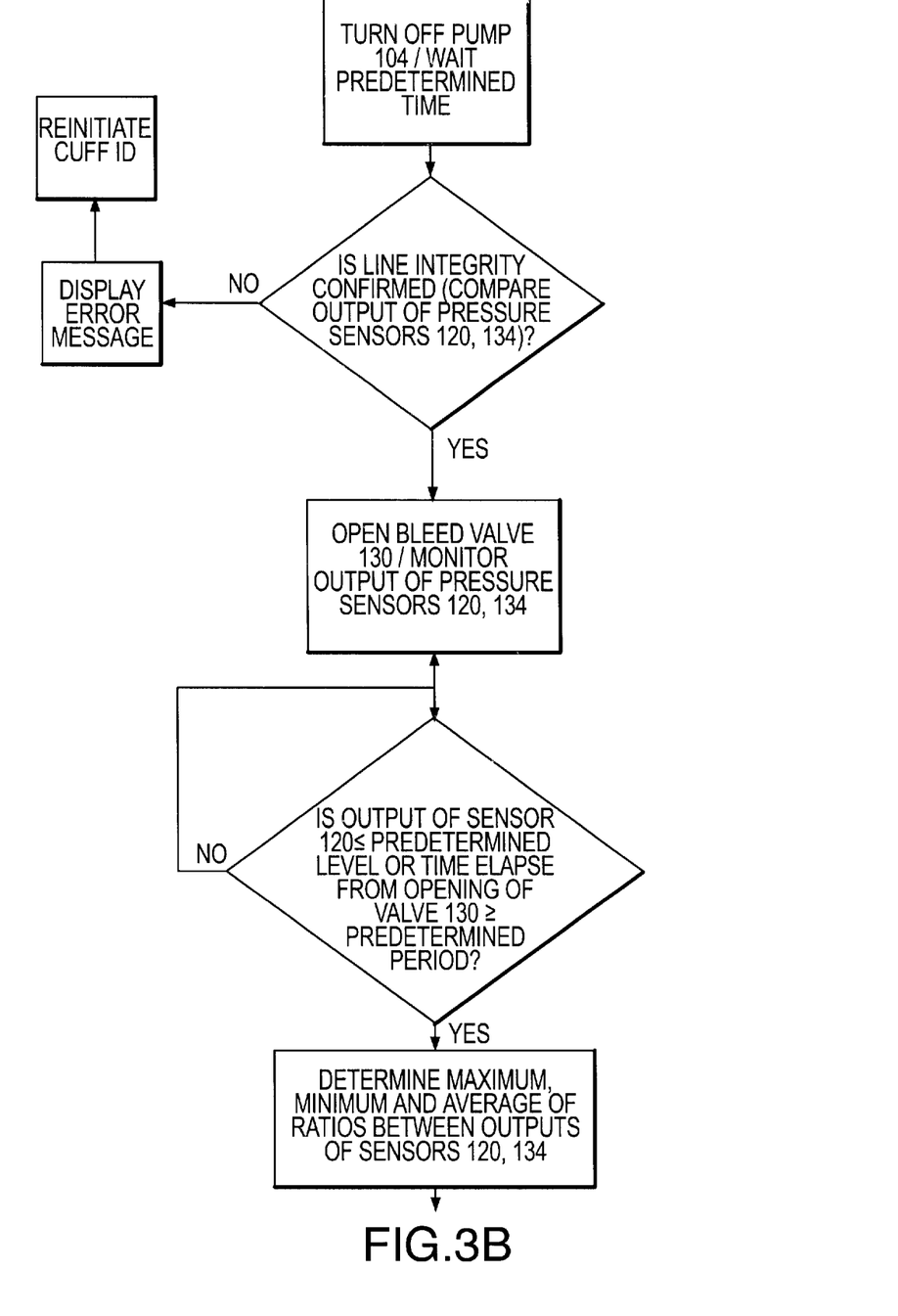
Figure 3C:
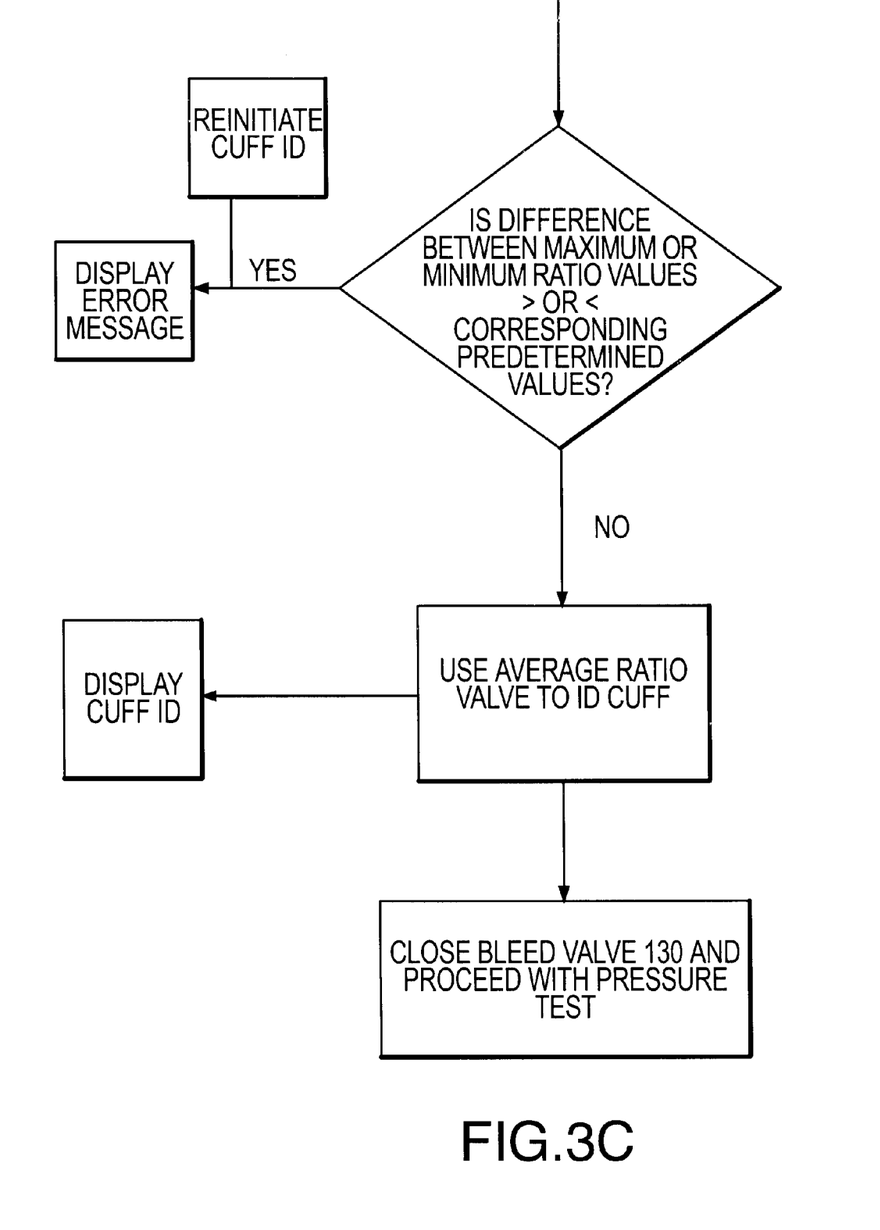

Operation of the illustrated embodiment will now be described with reference to FIGS. 3A–3C in combination with FIGS. 1 and 2. As will be appreciated, an automatic cuff identification operation will be normally initiated at the outset of a blood pressure measurement procedure, but prior to actual blood pressure measurement.

To initiate the procedure, monitor 100 is turned on, a given cuff assembly is secured to a patient (e.g. wrapping cuff 20 about the patient's arm), and cuff assembly 10 is pneumatically interconnected to monitor 100. For example, connector 40 may be directly interconnected with connector 102 of monitor 100, or connector 40 may be interconnected with connector 202 of a dual lumen hose 200, and connector 204 of the dual lumen hose 200 may be interconnected with connector 102 of monitor 100. Hose assembly 200 may be provided in a wide range of varying lengths.

In conjunction with the initial interconnections, the pneumatic inflation/deflation circuit is allowed to reach a quiescent state, wherein valves 116 and 130 are open and pump 104 is off. In this regard, it should be noted that monitor 100 may be provided so that a given cuff identification operation may be automatically undertaken upon start-up, or alternatively, so that such operation may be manually initiated via a user input at control 152 of monitor 100. Similarly, monitor 100 may be provided so that an initiated operation may be selectively overridden by a user via user input controls 152.

To ensure that the cuff 20 is adequately deflated for the identification procedure, one or more pressure readings may be taken at the first pressure sensor 120. More particularly, a plurality of pressure readings may be taken by sensor 120 (e.g. over a one second time period) and received by preprogrammed processor 146 for computation of a mean measured value. Such value may then be compared to a predetermined acceptable value (e.g. 20 torr). In the event that the measured value exceeds the predetermined acceptable value, the test may be repeated for a predetermined number of times and/or over a predetermined period. If the test is not passed, the automated cuff identification procedure may be automatically terminated and an error message may be displayed at the display output 150 of monitor 100.

Assuming the cuff deflation test is passed, processor 140 may then affect the closure of valves 116 and 130. Thereafter, processor 140 may transmit appropriate control signals to pump 104 so as to initiate the operation thereof in accordance with a predetermined, ramped drive protocol. By way of example, pump ramping may begin at a predetermined first duty cycle (e.g. 25%), and then increased by a predetermined percentage (e.g. 2%) for each predetermined time increment (e.g. each ten milliseconds) up to a maximum predetermined duty cycle (e.g. 100%). Such ramping function may reduce over-inflation instances associated with certain types of cuffs.

In conjunction with the ramped-up operation of pump 104, the second pressure sensor 134 may take pressure readings on an ongoing basis to monitor the pressure within the pneumatic circuit, and in particular the pressure downstream of cuff 20. As will be appreciated, such readings may be received by processor 140 for preprogrammed processing. When the pressure monitored by second pressure sensor 134 reaches a predetermined level (e.g. 50 torr), processor 140 may transmit control signals to terminate operation of pump 104. After the pump has been turned off, pneumatic circuit pressure may be allowed to equalized during a predetermined wait period (e.g. 0.5 seconds). During this period, valves 116 and 130 should remain closed.

After the delay, a test may be conducted to determine whether any of the pneumatic lines are blocked or may have a leak. Such test may be performed at processor 140 via a comparison of pressure readings taken by sensors 120 and 134 and received by processor 140. If the difference between the first and second sensor 120, 134 readings exceeds a predetermined level, such difference may indicate a blockage or a leak within the pneumatic circuit and an error message may be provided at display output 150. A user may then check for blockage or leakage, and depending upon the results of such investigation, may re-initiate the cuff identification operation or take other steps as may be appropriate in the given situation.

Assuming circuit line integrity is confirmed, processor 140 may then effect the opening of bleed valve 130 to a predetermined degree (e.g. a fully open position), while dump valve 116 is maintained in a closed state. Upon the opening of bleed valve 130, gas restrictor 128 provides a desired degree of gas flow resistance, thereby enhancing the measurement process (e.g., by normalizing the pressure reading to be taken). As previously noted, bleed valve 130 may be provided to function as restrictor 128, e.g., via controlled opening of the valve to a predetermined degree appropriate to establish the desired gas flow resistance. As gas is released from valve 130, pressure readings from both pressure sensor 120 and pressure sensor 134 may be obtained in synchronous pairs at processor 140 . Such pressure readings may be processed until the first of the following occurs:

i) the pressure monitored by first pressure sensor 120 drops below a predetermined level (e.g. 30 torr); or
  ii) a predetermined time period elapses from opening the bleed valve 130 (e.g. 0.5 seconds).

The above-noted pairs of pressure readings from the first sensor 120 and second sensor 134 may be processed by processor 140 to identify the given interconnected cuff 20. Such processing may provide for a comparison of the paired values. In one approach, such comparison may entail the computation of a ratio therebetween. In turn, the computed ratios for each of the plurality of synchronous pressure reading pairs may be employed to compute maximum, minimum and mean ratio values. As will be appreciated, such values will depend upon the degree of gas flow restriction through restrictor 32 of the given cuff assembly interconnected to monitor 100. As such, such values may be utilized by processor 140 (e.g. via reference to a predetermined look-up table stored at memory 142) to automatically identify which of the predetermined plurality of cuff assemblies is being employed.

In order to enhance the accuracy of cuff identification, processor 140 may be preprogrammed so that if a given mean ratio value falls between reference values corresponding with two different interconnectable cuff assemblies 10, processor may automatically provide for the display of an error message at display output 150 and/or a reinitiation of the cuff identification operation. More particularly, where a look-up table approach is employed for cuff identification at processor 140, "guard bands" may be utilized in the look-up table of predetermined reference values corresponding with the various predetermined plurality of cuff assemblies. For example, the look-up table may provide a plurality of non-overlapping ranges of reference values, wherein each of the ranges corresponds with one of a predetermined plurality of different sizes of cuff assemblies 10 (e.g. and corresponding different restrictors 32), and wherein the various ranges are separated by predetermined "guard bands". In the event that a given measured mean ratio value falls within a "guard band" of the look-up table, the processor 140 may be preprogrammed so as to provide an appropriate message at display output 150 and to reinitiate the cuff identification operation.

As noted, processor 140 may also compute maximum and minimum ratio values from the paired readings received from first sensor 120 and second sensor 134. Such maximum and minimum ratio values may be employed to reduce misidentification instances. In particular, processor 140 may be preprogrammed to compare the maximum and minimum ratio values and to determine whether a difference therebetween exceeds a predetermined threshold value. In this regard, it is recognized that wide variations between the maximum value and minimum value may indicate excessive patient motion during the cuff identification operation, which in turn may lead to an incorrect cuff identification. As such, the threshold value may be selected so that if the difference between the maximum and minimum ratio values exceeds such threshold value, an error message is displayed at display output 150 and/or the cuff identification operation is reinitiated.

Upon identification of a given cuff assembly 10, the processor 140 may effect closure of bleed valve 130 and then further select a predetermined protocol stored at memory 142 for use in a subsequent blood pressure measurement procedure. For example, such protocol may provide for the inflation of the interconnected cuff assembly 10 to a predetermined pressure level determined to be most appropriate for the given type of interconnected cuff assembly 10.

As previously noted, the described embodiment is particularly apt for use in identifying which of a plurality of cuff assemblies is interconnected to monitor 100, wherein such predetermined plurality of cuff assemblies comprises a group consisting of two or more of the following:

i) an arm cuff intended for a very large adult/obese patient;
  ii) an arm cuff intended for an average adult;
  iii) an arm cuff intended for a child; and
  iv) an arm cuff intended for use on a neonate.

In such an application, it will be appreciated that each of the different intended cuff applications will correspond with a different size cuff 20 in the corresponding cuff assembly 10. For each of such different sized cuffs 20, a different set of pressure settings may be appropriate for conducting the blood pressure monitoring procedure. In particular, initial pressure settings for the blood pressure monitoring procedure may be set as follows:

i) for a very large adult/obese patient the initial inflation pressure should equal at least approximately 200 mmHg, with a safety maximum of about 300 mmHg;
  ii) for average adult the initial inflation pressure should equal approximately 160 mmHg, with a safety maximum of about 300 mmHg;
  iii) for child the initial inflation pressure should equal approximately 160 mmHg, with a safety maximum of about 215 mmHg; and
  iv) for neonate the initial inflation pressure should equal no more than approximately 120 mmHg, with a safety maximum of about 150 mmHg.

The embodiment description provided above is for purposes of facilitating an understanding of the present invention and is not intended to limit the scope in any way. Numerous modifications, adaptations and extensions will be apparent to those skilled in the art and are intended to be within the scope of the present invention as defined by the claims that follow.

What is claimed is:

1. A method for identifying an inflatable cuff for blood pressure measurement, said inflatable cuff being interconnected to a first gas-flow restrictor, comprising:

inflating, at least partially, said inflatable cuff by flowing a gas thereinto free from passage through said interconnected first gas-flow restrictor;

deflating, at least partially, the inflatable cuff by passing at least a portion of said gas out of said inflated cuff and through said interconnected first gas-flow restrictor;

obtaining, during said deflating step, at least one gas pressure measurement at a location pneumatically interconnected with said inflatable cuff; and identifying said inflatable cuff using said at least one pressure measurement.

2. The method of claim 1, wherein a first pressure measurement means is employed to obtain said at least one gas pressure measurement downstream of said inflatable cuff.

3. The method of claim 2, wherein said first gas-flow restrictor is downstream from said inflatable cuff, and further comprising:

obtaining, during said deflating step, at least another gas pressure measurement at a location pneumatically interconnected with and upstream from said inflatable cuff for use in said identifying step.

4. The method of claim 3, wherein said deflating step further comprises:

passing said gas through a second gas-flow restrictor pneumatically interconnected with said inflatable cuff downstream from said first pressure measurement means.

5. The method of claim 4, wherein said deflating step further comprises:

selectively opening a bleed valve pneumatically interconnected with said inflatable cuff downstream from said second gas-flow restrictor.

6. The method of claim 1, wherein said inflatable cuff is one of a predetermined plurality of inflatable cuffs, and wherein each of said plurality of inflatable cuffs is interconnected to a corresponding one of a plurality of gas-flow restrictors.

7. The method of claim 1, wherein in said inflating step said inflatable cuff is inflated to a first degree corresponding with a first predetermined pressure.

8. The method of claim 7, further comprising:

utilizing a pressure measurement means, pneumatically interconnected with said inflatable cuff, to determine when said first predetermined pressure is reached.

9. The method of claim 8, wherein in said deflating step said inflatable cuff is deflated to at least a second degree corresponding with a second predetermined pressure.

10. The method of claim 9, wherein said obtaining step is terminated based upon at least one of the following conditions:

when said second predetermined pressure is reached; and
when a predetermined amount of time elapses after initiation of said deflating step.

11. The method of claim 9, wherein said obtaining step is terminated upon the earliest of the following conditions:

when said second predetermined pressure is reached; and
when a predetermined amount of time elapses after initiation of said deflating step.

12. The method of claim 1, wherein said at least one gas pressure measurement is obtained downstream of the inflatable cuff and further comprising:

conducting at least another gas pressure measurement upstream of said inflatable cuff;
determining a value corresponding with a ratio between said at least one gas pressure measurement downstream of said inflatable cuff and said at least another pressure measurement up stream of said inflatable cuff; and
using said value in said identifying step.

13. The method of claim 1, wherein in said obtaining step a plurality of pressure measurements are obtained downstream of said inflatable cuff, and further comprising:

conducting a plurality of pressure measurements upstream of said inflatable cuff in synchronous, one-to-one relation with said plurality of pressure measurements obtained downstream of said inflatable cuff, wherein a plurality of pairs of upstream and downstream gas pressure measurements are obtained.

14. The method of claim 13, further comprising:

determining a plurality of values corresponding with ratios between each given pair of said downstream and upstream gas pressure measurements, wherein said plurality of values are employed in said identifying step.

15. The method of claim 14, further comprising:

calculating an average of said plurality of values for use in said identifying step.

16. The method of claim 15, further comprising:

identifying a maximum value and a minimum value of said plurality of values.

17. The method of claim 16, further comprising:

comparing said maximum value and said minimum value with a corresponding maximum reference value and corresponding minimum reference value, respectively; and providing an automatic response when said maximum value exceeds said corresponding maximum reference value or said minimum value is less than the corresponding minimum reference value.

18. The method of claim 17, wherein said automatic response is at least one of an alarm indication to a user, an automatic verification of the method, and an automatic termination of the method.

19. The method of claim 1, wherein said inflating step comprises:

pumping air into said inflatable cuff at a predetermined ramped rate.

20. The method of claim 1, further comprising:

waiting a predetermined time period between a termination of said inflating step and an initiation of said deflating step; and taking, during said waiting step, an upstream gas pressure measurement upstream of said inflatable cuff and a downstream pressure measurement downstream of said inflatable cuff; and comparing said upstream pressure measurement and downstream pressure measurement.

21. The method of claim 20, further comprising:

providing an automatic response when said comparison between said upstream pressure measurement and downstream pressure measurement indicates a difference therebetween that exceeds a predetermined reference value.

22. The method of claim 1, wherein said inflating, deflating, obtaining and identifying steps are each initiated and completed under the control of a processor in accordance with a preprogrammed algorithm.

23. The method for claim 1, further comprising:

automatically selecting a predetermined inflation value for use in a blood pressure measurement procedure based upon the identification of said inflatable cuff.

24. An apparatus for identifying at least one inflatable cuff interconnectable to a sphygmomanometer, said inflatable cuff being directly interconnected to a first gas-flow restrictor, comprising:

inflation means, interconnectable in a pneumatic circuit to said inflatable cuff, for selectively inflating the inflatable cuff by passing a gas thereinto free from passage through said interconnected first gas-flow restrictor;

deflation means, interconnectable in a pneumatic circuit to said inflatable cuff, for selectively deflating the inflatable cuff by passing at least a portion of said gas out of said inflatable cuff and through said interconnected first gas-flow restrictor;

first pressure measurement means, pneumatically interconnected to said deflation means, for obtaining at least one gas pressure measurement in said pneumatic circuit downstream of said interconnectable inflatable cuff; and processor means, operatively interconnected with said first pressure measurement means, for automatically causing said pressure measurement means to obtain said at least one pressure measurement during operation of said deflation means, and for employing said at least one pressure measurement to identify said at least one inflatable cuff when interconnected to the apparatus.

25. The apparatus of claim 24, wherein said processor means is operatively interconnected with said inflation means and said deflation means to control the operation of said inflation means and deflation means.

26. An apparatus as claimed in claim 25, said inflation means comprising:

an air pump interconnected in said pneumatic circuit upstream from the interconnected inflatable cuff; and, said deflation means comprising:

a bleed valve interconnected in said pneumatic circuit downstream from the interconnected cuff, wherein said processor is preprogrammed to selectively operate said air pump, and to selectively open and close said bleed valve in accordance with a preprogrammed cuff identification algorithm.

27. An apparatus as recited in claim 26, further comprising:

second pressure measurement means, pneumatically interconnected to said inflation means, for obtaining at least one pressure measurement in said pneumatic circuit upstream of said interconnectable inflatable cuff.

28. An apparatus as claimed in claim 27, wherein said processor is operable to automatically receive said at least one upstream pressure measurement and said at least one downstream pressure measurement and to automatically determine a ratio value therebetween.

29. The apparatus of claim 27, wherein said processor is preprogrammed to automatically receive a plurality of upstream pressure measurements from said first pressure measurement means and a corresponding plurality of downstream pressure measurements from said second pressure measurement means to yield a corresponding plurality of upstream and downstream values.

30. The apparatus of claim 29, wherein said processor is preprogrammed to calculate a ratio between the upstream pressure measurement and downstream pressure measurement comprising each pair of values for use in the identification of said at least one inflatable cuff.

31. The apparatus of claim 24, wherein said inflation means, deflation means, first pressure measurement means and processor means are located in a common housing.

32. The apparatus of claim 24, wherein said interconnectable inflatable cuff is fixedly and pneumatically attached to a first gas-flow restricting means for restricting the passage of gas therethrough.

33. The apparatus of claim 32, wherein said deflation means comprises:

a second gas-flow restriction means for restricting the passage of gas therethrough.

34. The apparatus of claim 24, wherein said apparatus is operable to identify a given one of a predetermined plurality of inflatable cuffs interconnectable to a sphygmomanometer, wherein each of said predetermined plurality of inflatable cuffs is fixedly and pneumatically interconnected to a corresponding one of a plurality of gas-flow restricting means, each of said gas-flow restricting means being different, and wherein said processor means is operable to identify a given one of said predetermined plurality of inflatable cuffs when said given one is interconnected to the apparatus.

35. A system for use in obtaining blood pressure measurements comprising:

a predetermined plurality of inflatable cuffs, each of said predetermined plurality of inflatable cuffs being fixedly and pneumatically interconnected to a corresponding one of a plurality of gas-flow restricting means, wherein each of said plurality of gas-flow restricting means restrict the flow of gas therethrough to a differing degree; and a monitor, pneumatically interconnectable to any one of said predetermined plurality of inflatable cuffs, including inflation means for selectively inflating a given, interconnected one of said predetermined plurality of inflatable cuffs and deflation means for selectively deflating said given, interconnected one of said predetermined plurality of inflatable cuffs, wherein said monitor is operable to automatically identify said given, interconnected one of said predetermined plurality of inflatable cuffs based upon at least one pressure measurement obtained during operation of said deflation means.

36. The system of claim 35, wherein said monitor further includes:

first pressure measurement means for obtaining pressure measurements upstream of said given, interconnected one of said predetermined plurality of inflatable cuffs; and a second pressure measurement means for obtaining pressure measurements downstream from said given, interconnected one of said predetermined plurality of inflatable cuffs.

37. The system of claim 36, further comprising:

a processor for automatically controlling operation of said inflation means, deflation means, first pressure measurement means and second pressure measurement means according to a pre-programmed cuff identification algorithm.

* * * * *